(12) United States Patent
Kim et al.

(10) Patent No.: US 11,865,211 B2
(45) Date of Patent: Jan. 9, 2024

(54) NANOPARTICLE COMPLEX SHOWING IMPROVED CELLULAR UPTAKE THROUGH SURFACE MODIFICATION USING LIPID AND MANUFACTURING METHOD THEREFOR

(71) Applicant: SOGANG UNIVERSITY RESEARCH FOUNDATION, Seoul (KR)

(72) Inventors: Hyun Cheol Kim, Seoul (KR); Do Yeon Kim, Seoul (KR)

(73) Assignee: INSBIOPHARM CO., LTD.

( * ) Notice: Subject to any disclaimer, the term of this patent is extended or adjusted under 35 U.S.C. 154(b) by 0 days.

(21) Appl. No.: 17/056,402

(22) PCT Filed: Sep. 4, 2018

(86) PCT No.: PCT/KR2018/010309
§ 371 (c)(1),
(2) Date: Nov. 17, 2020

(87) PCT Pub. No.: WO2019/231051
PCT Pub. Date: Dec. 5, 2019

(65) Prior Publication Data
US 2021/0308050 A1 Oct. 7, 2021

(30) Foreign Application Priority Data
Jun. 1, 2018 (KR) .................. 10-2018-0063163

(51) Int. Cl.
*A61K 9/127* (2006.01)
*A61K 9/50* (2006.01)
(Continued)

(52) U.S. Cl.
CPC .......... *A61K 9/1271* (2013.01); *A61K 9/1277* (2013.01); *A61K 9/5015* (2013.01);
(Continued)

(58) Field of Classification Search
CPC .................................................. A61K 9/1271
See application file for complete search history.

(56) References Cited

U.S. PATENT DOCUMENTS

2021/0177756 A1* 6/2021 Noy ..................... A61K 31/704

FOREIGN PATENT DOCUMENTS

KR   10-2014-0052812 A    5/2014
KR   10-2016-0135424 A    11/2016
(Continued)

OTHER PUBLICATIONS

R. Kotitz, W. Weitschies, L. Trahms, W. Brewer, and W. Semmler. "Determination of the binding reaction between avidin and biotin by relaxation measurements of magnetic nanoparticles." Journal of Magnetism and Magnetic Materials, vol. 194 (1999), pp. 62-68. (Year: 1999).*

(Continued)

*Primary Examiner* — Isaac Shomer
(74) *Attorney, Agent, or Firm* — GOLDILOCKS ZONE IP LAW

(57) ABSTRACT

The present disclosure relates to a nanoparticle complex that is taken into cells to be used for the treatment of diseases, and a method of manufacturing the same using a top-down process. In the top-down process, surfaces of nanoparticles are modified with a lipid-based material having high stability and excellent biocompatibility, thereby improving endocytosis efficiency. A lipid structure having a tube shape is bonded to a portion of the surface of the nanoparticle, so that the nanoparticle complex undergoes endocytosis, directly penetrates a cell membrane, and is effectively taken into spheroid-type tumor cells. The lipid structure is not directly attached to the nanoparticles, lipid-based lipidomes (such as bubbles and liposomes) are bonded to the nanoparticles, and mechanical force is applied thereto to thus crush the lipidomes, so that the lipid structure is formed on the surface of the nanoparticle.

2 Claims, 9 Drawing Sheets
(4 of 9 Drawing Sheet(s) Filed in Color)
Specification includes a Sequence Listing.

(51) Int. Cl.
    *A61K 9/51*         (2006.01)
    *A61K 31/704*     (2006.01)
    *A61K 31/7105*    (2006.01)

(52) U.S. Cl.
    CPC .......... *A61K 9/5089* (2013.01); *A61K 9/5192* (2013.01); *A61K 31/704* (2013.01); *A61K 31/7105* (2013.01)

(56) References Cited

FOREIGN PATENT DOCUMENTS

| | | | |
|---|---|---|---|
| KR | 10-2017-0040748 A | 4/2017 | |
| WO | WO-2014021678 A1 * | 2/2014 | ........... A61K 31/337 |
| WO | 2015/153805 A2 | 10/2015 | |
| WO | WO-2017041033 A1 * | 3/2017 | ............. A61K 47/62 |
| WO | 2018/064350 A1 | 4/2018 | |

OTHER PUBLICATIONS

Exelead. "Liposomes and Lipid Nanoparticles as Delivery Vehicles for Personalized Medicine." https://www.exeleadbiopharma.com/news/liposomes-and-lipid-nanoparticles-as-delivery-vehicles-for-personalized-medicine accessed Apr. 13, 2018, originally published Nov. 16, 2018, pp. 1-18. (Year: 2018).*

Google Patents. English Translation of WO 2014021678 A1. Obtained at https://patents.google.com/patent/WO2014021678A1/en?oq=WO+2014%2f021678 on Jun. 24, 2022, originally published in Korean in 2014, 18 printed pages. (Year: 2014).*

* cited by examiner

[FIG.1]
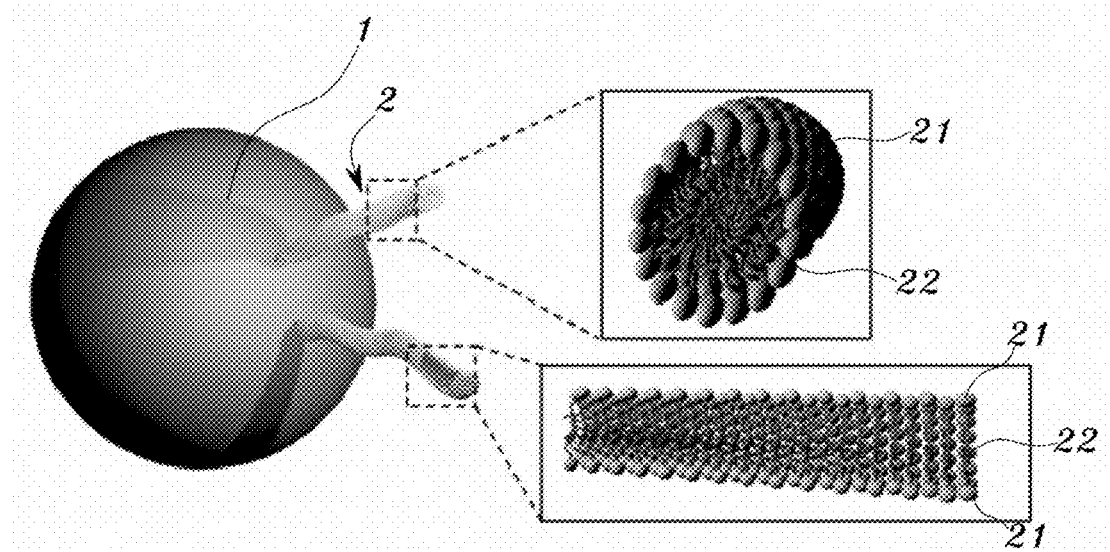
[FIG.2]
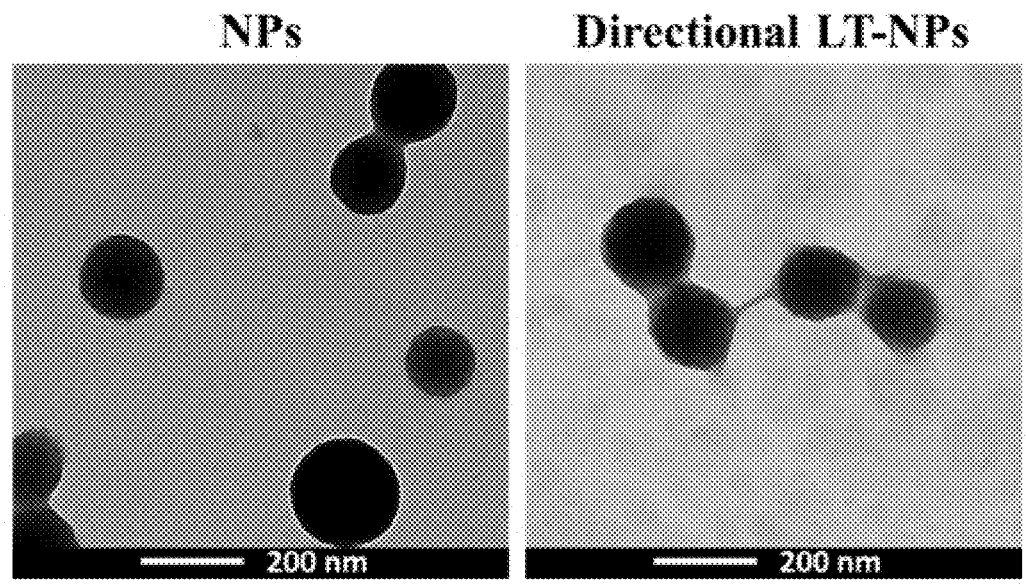

[FIG.3]
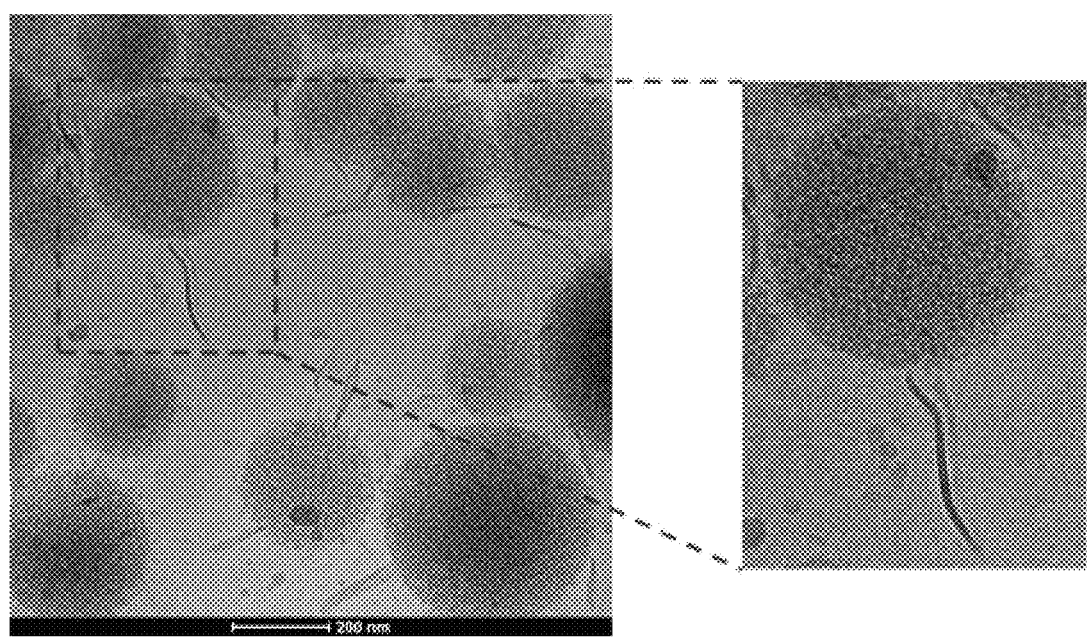

[FIG.4]
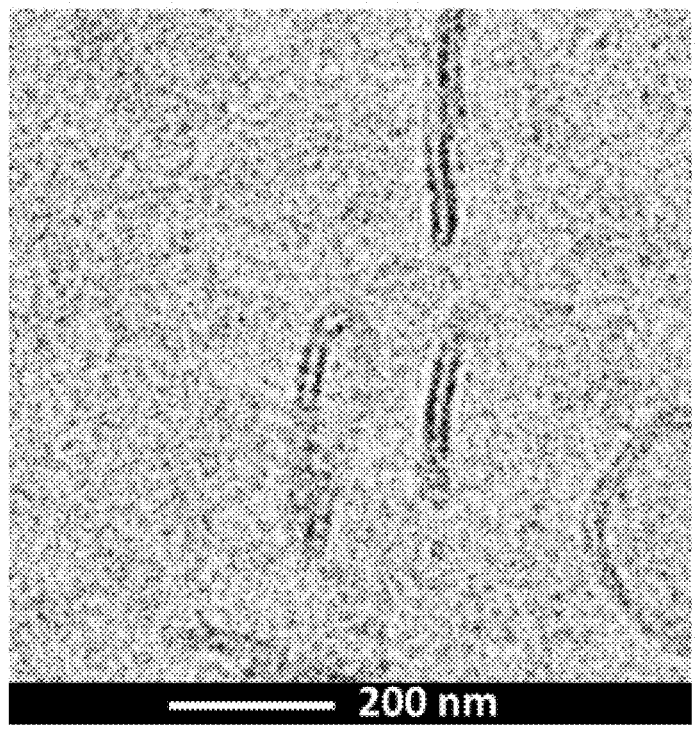
[FIG.5]
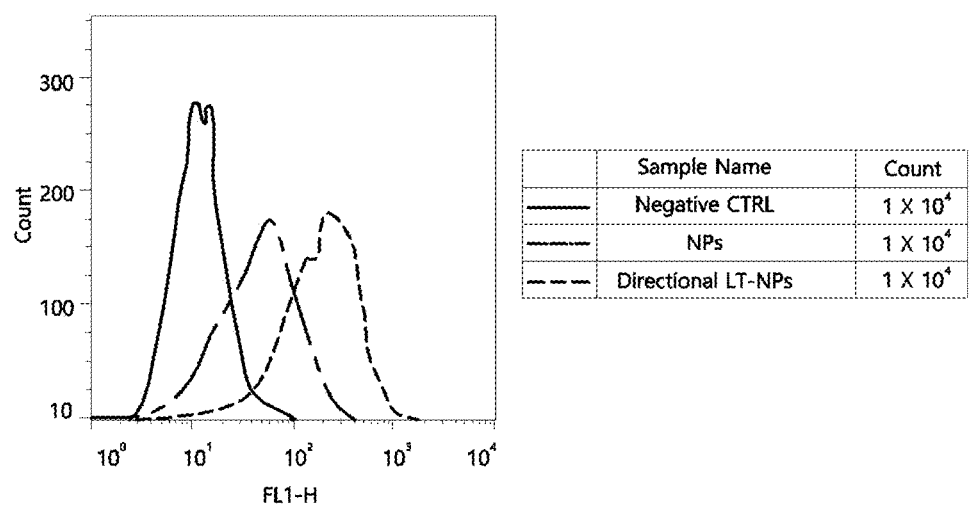

[FIG.6]
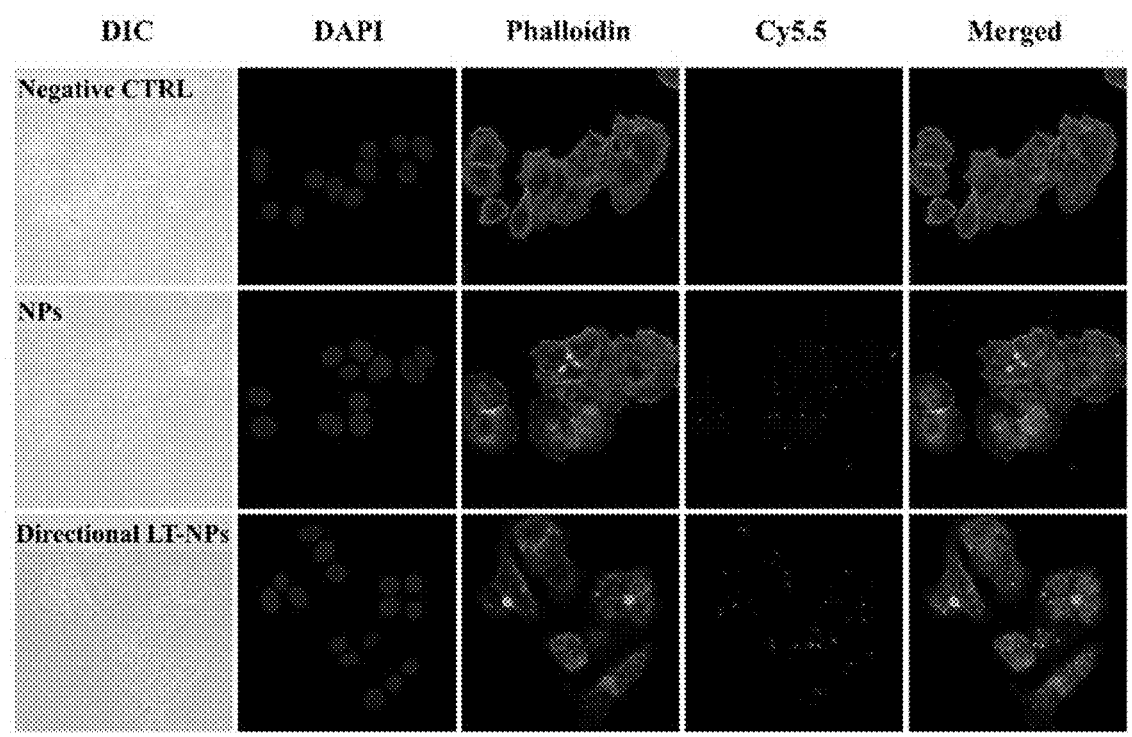

[FIG.7]
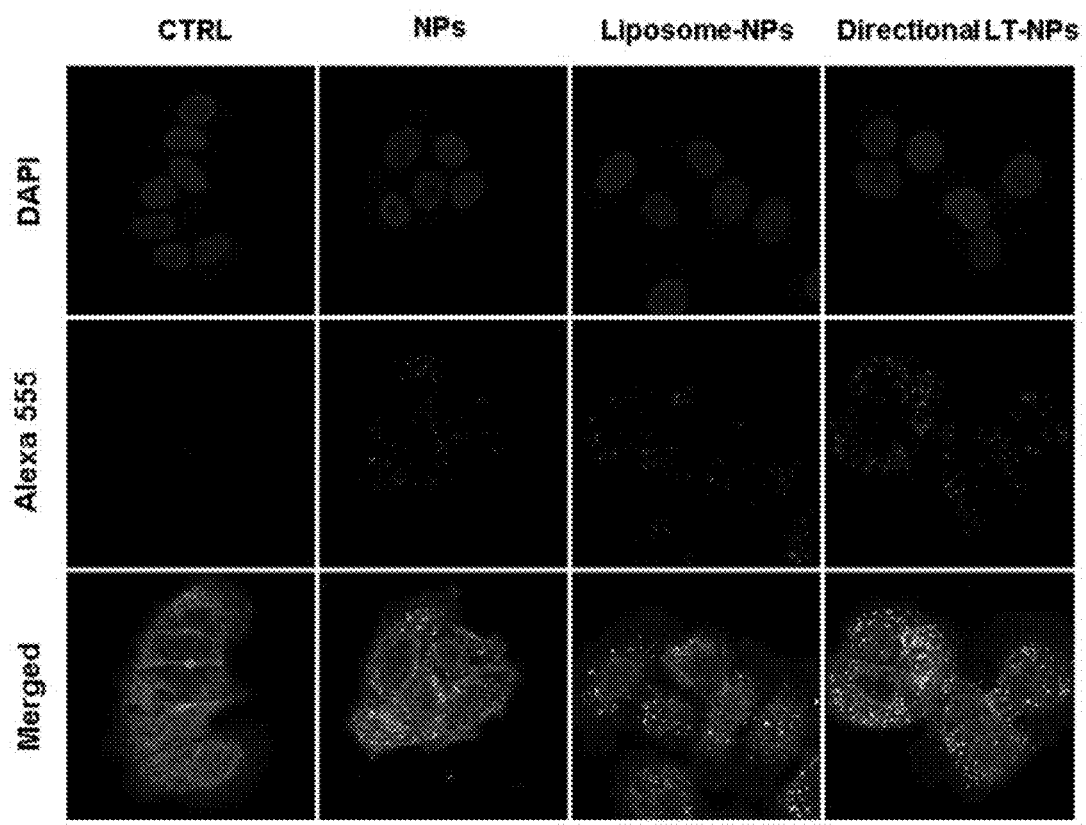

[FIG.8]
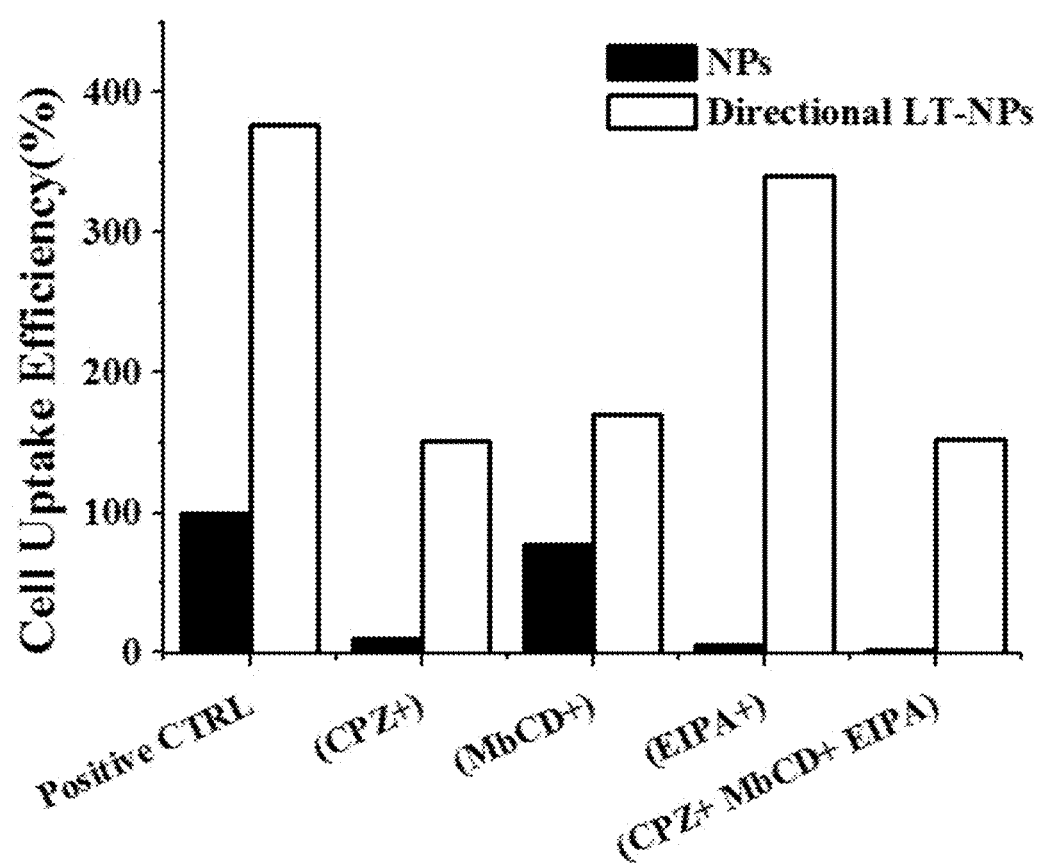

[FIG.9]
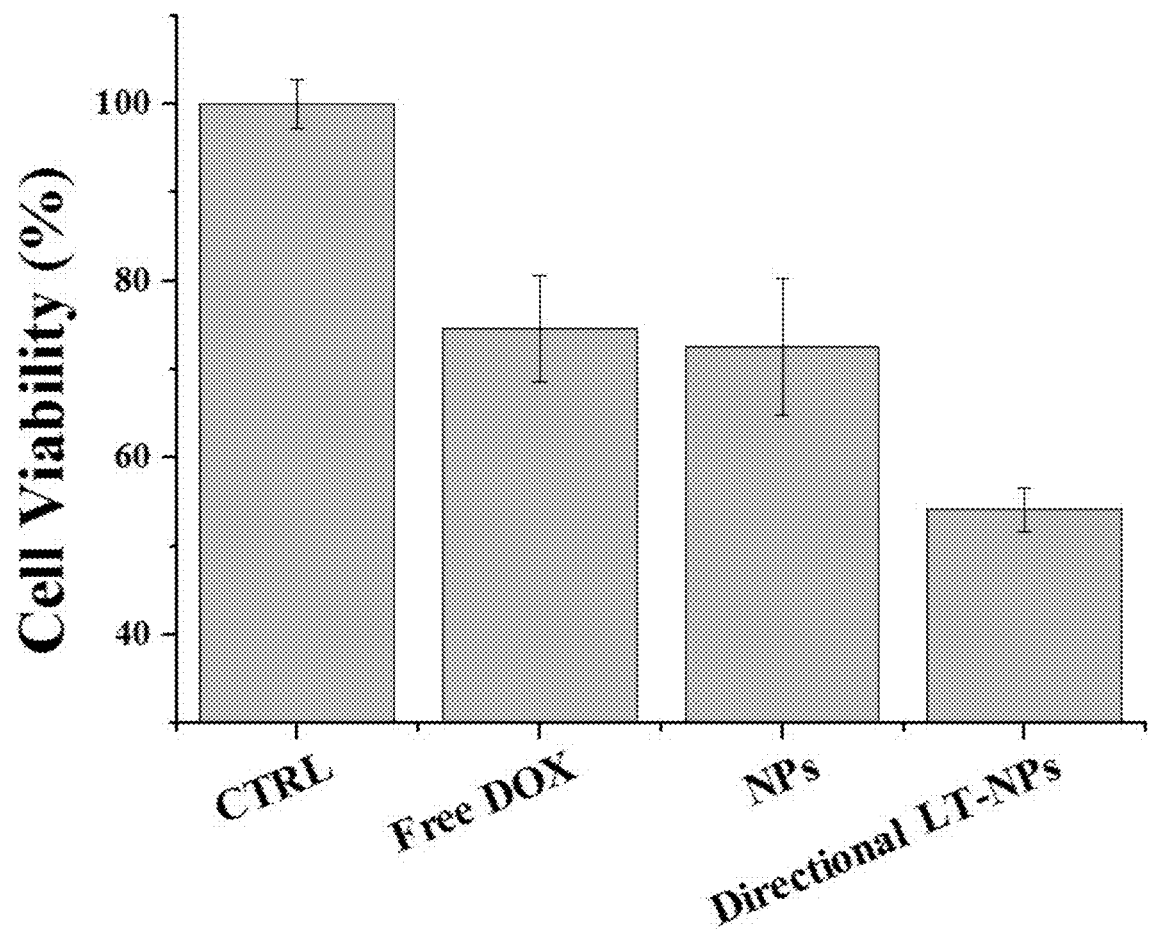

[FIG.10]
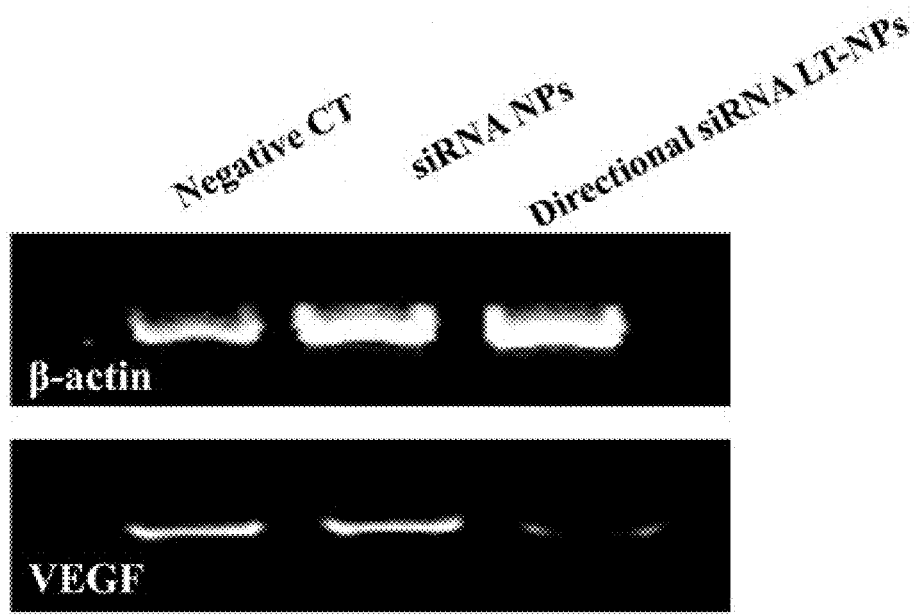
[FIG.11]
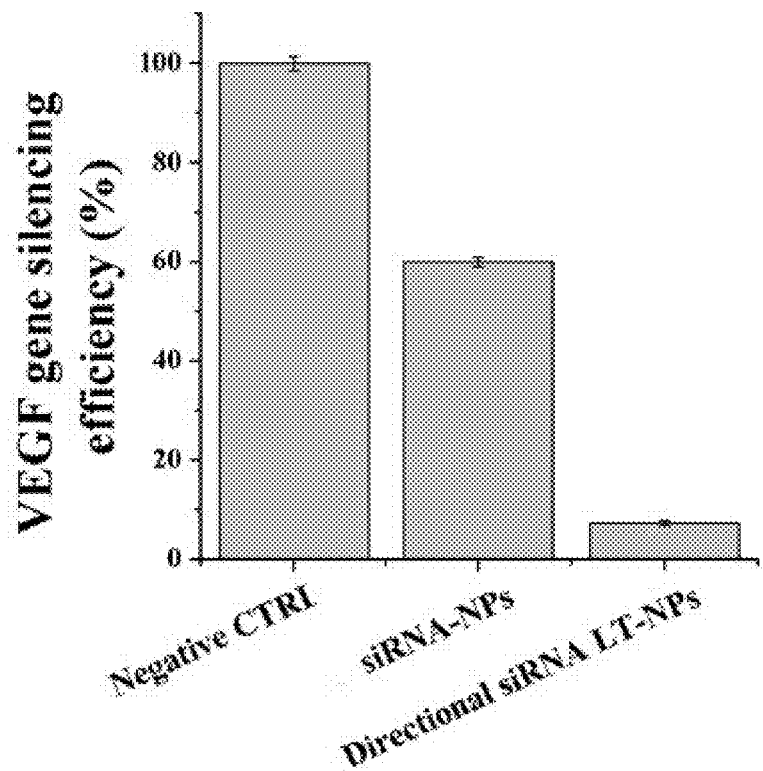

[FIG.12]
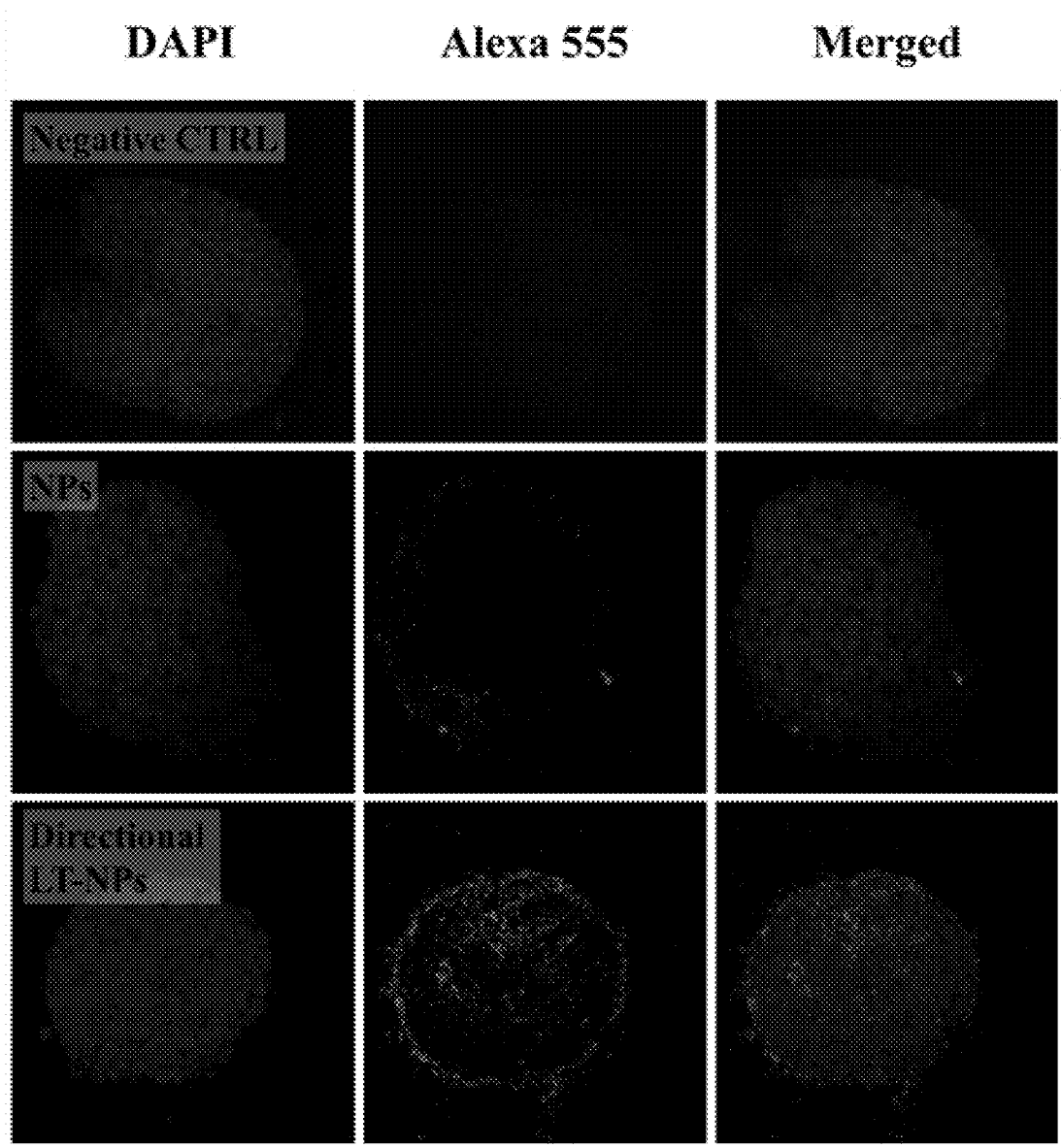

NANOPARTICLE COMPLEX SHOWING IMPROVED CELLULAR UPTAKE THROUGH SURFACE MODIFICATION USING LIPID AND MANUFACTURING METHOD THEREFOR

CROSS-REFERENCE TO RELATED APPLICATIONS

This application claims the benefit under 35 U.S.C. section 371, of PCT International Application No.: PCT/KR2018/010309, filed on Sep. 4, 2018, which claims foreign priority to Korean Patent Application No.: KR10-2018-0063163, filed on Jun. 1, 2018, in the Korean Intellectual Property Office, both of which are hereby incorporated by reference in their entireties.

TECHNICAL FIELD

The present disclosure relates to a nanoparticle complex that is taken into cells to be used for the treatment of disease, and a method of manufacturing the same. More particularly, the present disclosure relates to a nanoparticle complex and a method of manufacturing the same using a top-down process. In the top-down process, surfaces of nanoparticles are modified with a lipid-based material having high stability and excellent biocompatibility, thereby improving cellular uptake. A lipid structure having a tube shape is bonded to a portion of the surface of the nanoparticle, so that the nanoparticle complex undergoes endocytosis, directly penetrates a cell membrane, and is effectively taken into spheroid-type tumor cells. The lipid structure is not directly attached to the nanoparticle, lipid-based lipidomes (such as bubbles and liposomes) are bonded to the nanoparticles, and mechanical force is applied thereto to thus crush the lipidomes, so that the lipid structure is formed on the surface of the nanoparticle. Since a top-down process is used, it is possible to easily mass-produce the nanoparticle complex.

BACKGROUND ART

In the field of drug delivery, cellular uptake is an important measure for achieving drug delivery efficacy. Therefore, technology for achieving improvement in cellular uptake has been widely developed. For example, as described in the following patent document, there is an effort to improve the cellular uptake of nanoparticles by chemically bonding a cell-permeable peptide to the nanoparticles.

PATENT DOCUMENT

Korean Laid-Open Patent Application No. 10-2017-0040748 (published on 2017. Apr. 13) "Drug delivery system and self-assembled nanostructure including multi-block polypeptide"

However, the conventional technology for achieving an improvement in cellular uptake cannot obtain a sufficient effect, and there is a problem in that the bonded materials are easily decomposed and thus stability is poor.

DISCLOSURE

Technical Problem

Accordingly, the present disclosure has been made keeping in mind the above problems occurring in the related art, and an objective of the present disclosure is to provide a nanoparticle complex in which surfaces of nanoparticles are modified with a lipid-based material having high stability and excellent biocompatibility, thereby dramatically improving cellular uptake, and a method of manufacturing the same.

Another objective of the present disclosure is to provide a nanoparticle complex in which a lipid structure having a tube shape is bonded to a portion of the surface of a nanoparticle, so that the nanoparticle complex undergoes endocytosis (a mechanism by which particles having a size of 100 to 200 nm are taken into cells) and directly penetrates a cell membrane, and a method of manufacturing the same.

Another objective of the present disclosure is to provide a nanoparticle complex which is capable of effectively taking nanoparticles into spheroid-type tumor cells due to the tissue penetration ability thereof.

Another objective of the present disclosure is to provide a nanoparticle complex and a method of manufacturing the same using a top-down process. In the process, a lipid structure is not directly attached to a nanoparticle, lipid-based lipidomes (such as bubbles and liposomes) are bonded to the nanoparticles, and mechanical force is applied thereto to thus crush the lipidomes, so that the lipid structure is formed on the surface of the nanoparticle. Since a top-down process is used, it is possible to easily mass-produce the nanoparticle complex.

Technical Solution

The present disclosure is implemented by embodiments having the following constitution in order to achieve the above objectives.

According to an embodiment of the present disclosure, a nanoparticle complex according to the present disclosure includes a nanoparticle that is taken into cells to be used for the treatment of disease, and a lipid-based lipid structure that is bonded to a portion of the outer surface of the nanoparticle, thus improving the cellular uptake of the nanoparticle.

According to another embodiment of the present disclosure, in the nanoparticle complex according to the present disclosure, the nanoparticle has a diameter of 100 to 300 nm, and the lipid structure has a length of 50 to 300 nm and a width of 3 to 20 nm.

According to another embodiment of the present disclosure, in the nanoparticle complex according to the present disclosure, the lipid structure has a long tube shape in which a lipid head having hydrophilicity is positioned at an outer side thereof and a lipid tail having hydrophobicity is positioned at an inner side thereof.

According to another embodiment of the present disclosure, in the nanoparticle complex according to the present disclosure, the nanoparticle includes a first reactive group, the lipid structure includes a second reactive group chemically bonded to the first reactive group of the nanoparticle, and the first reactive group and the second reactive group are chemically bonded to each other, thus bonding the lipid structure to the nanoparticle.

According to another embodiment of the present disclosure, in the nanoparticle complex according to the present disclosure, the nanoparticle includes the first reactive group positioned on an outer surface thereof, the lipid structure having the tube shape includes the second reactive group positioned at an end thereof, and the first reactive group and the second reactive group are chemically bonded to each other, thus bonding the lipid structure having the tube shape to the outer surface of the nanoparticle.

According to another embodiment of the present disclosure, in the nanoparticle complex according to the present disclosure, the nanoparticle includes a material capable of carrying a drug or treating diseases.

According to another embodiment of the present disclosure, in the nanoparticle complex according to the present disclosure, the nanoparticle complex is taken into cells by endocytosis and by directly penetrating the cell membrane.

According to another embodiment of the present disclosure, in the nanoparticle complex according to the present disclosure, the lipid structure improves penetration of nanoparticles into the tissues of spheroid-type tumor cells.

According to another embodiment of the present disclosure, in the nanoparticle complex according to the present disclosure, the nanoparticles include an anticancer drug and improve an efficiency of killing tumor cells.

According to another embodiment of the present disclosure, a method of manufacturing a nanoparticle complex according to the present disclosure includes a nanoparticle-forming step of forming nanoparticles including a first reactive group, a lipidome-forming step of forming phospholipid-based lipidomes having a micro size including a second reactive group chemically bonded to the first reactive group, a lipid-complex-forming step of mixing the nanoparticles and the lipidomes so that the first reactive group and the second reactive group are bonded to each other, thus forming a lipidome-nanoparticle complex in which the nanoparticles are bonded to outer sides of the lipidomes, and a crushing formation step of applying mechanical force to the lipidome-nanoparticle complex formed in the lipid-complex-forming step so that the lipidomes are crushed to form a lipid structure bonded to a portion of an outer surface of the nanoparticle, thus manufacturing the nanoparticle complex. The lipidomes are bubbles or liposomes, the nanoparticles are taken into cells to be used for treatment of disease, and the lipid structure improves the cellular uptake of the nanoparticle.

According to another embodiment of the present disclosure, in the method of manufacturing a nanoparticle complex according to the present disclosure, in the crushing formation step, the mechanical force is applied to the lipidome-nanoparticle complex and maintained for a predetermined period of time, so that the lipidomes are crushed and phospholipids forming the lipidomes are recombined, thus forming the lipid structure having a tube shape bonded to the nanoparticle.

Advantageous Effects

The present disclosure may obtain the following effects by the above embodiments.

In the present disclosure, surfaces of nanoparticles are modified with a lipid-based material having high stability and excellent biocompatibility, thereby dramatically improving cellular uptake.

Further, in the present disclosure, a lipid structure having a tube shape is bonded to a portion of the surface of a nanoparticle, so that a nanoparticle complex undergoes endocytosis (a mechanism by which particles having a size of 100 to 200 nm are taken into cells) and directly penetrates a cell membrane.

Further, in the present disclosure, it is possible to effectively take nanoparticles into spheroid-type tumor cells due to the tissue penetration ability thereof.

Further, in the present disclosure, a top-down process is used, in which a lipid structure is not directly attached to a nanoparticle, lipid-based lipidomes (such as bubbles and liposomes) are bonded to the nanoparticles, and mechanical force is applied thereto to thus crush the lipidomes, so that the lipid structure is formed on the surface of the nanoparticle. Accordingly, it is possible to easily mass-produce a nanoparticle complex.

DESCRIPTION OF DRAWINGS

The patent or application file contains at least one drawing executed in color. Copies of this patent or patent application publication with color drawing(s) will be provided by the Office upon request and payment of the necessary fee.

FIG. 1 is a schematic view of a nanoparticle complex according to an embodiment of the present disclosure;

FIG. 2 is TEM images of a nanoparticle complex according to an embodiment of the present disclosure;

FIG. 3 is Cryo-TEM images of a nanoparticle complex according to an embodiment of the present disclosure;

FIG. 4 is a Cryo-TEM image of a lipid structure bonded to a nanoparticle complex according to an embodiment of the present disclosure;

FIG. 5 is a chart showing the analysis results obtained using flow cytometry to check the cell uptake efficiency of a nanoparticle complex according to an embodiment of the present disclosure;

FIGS. 6 and 7 are confocal microscope images for confirming the cell uptake efficiency of a nanoparticle complex according to an embodiment of the present disclosure;

FIG. 8 is a chart showing the analysis results obtained using flow cytometry to check the cell uptake efficiency of a nanoparticle complex according to an embodiment of the present disclosure after treatment with an endocytosis inhibitor;

FIG. 9 is a chart showing the results of a cell viability assay for confirming the efficacy of a nanoparticle complex according to an embodiment of the present disclosure as an anticancer drug delivery system;

FIGS. 10 and 11 are views showing the results of gene silencing for confirming the efficacy of a nanoparticle complex according to an embodiment of the present disclosure as a genome drug delivery system; and FIG. 12 is confocal microscope images for confirming the cell uptake efficiency of a nanoparticle complex according to an embodiment of the present disclosure in a spheroid tumor cell model.

DESCRIPTION OF THE REFERENCE
NUMERALS USED IN THE DRAWINGS

| | |
|---|---|
| 1: Nanoparticle | 2: Lipid structure |
| 21: Lipid head | 22: Lipid tail |

BEST MODE

Hereinafter, a nanoparticle complex having improved cellular uptake through surface modification using lipids according to the present disclosure and a method of manufacturing the same will be described in detail with reference to the accompanying drawings. Unless otherwise defined, all terms in the present specification have the same general meanings as understood by those of ordinary skill in the art to which the present disclosure belongs. If the terms conflict with the meanings of the terms used in the present specification, the definition used in the present specification is to be applied. Further, detailed descriptions of known functions and configurations that may unnecessarily obscure the subject matter of the present disclosure will be omitted. Throughout the specification, when a part is said to "include" a certain component, it means that other components may be further included, rather than excluding other components, unless otherwise stated.

A nanoparticle complex having improved cellular uptake through surface modification using lipids according to an embodiment of the present disclosure will be described with reference to FIGS. 1 to 12. The nanoparticle complex includes a nanoparticle 1 that is taken into cells to be used for treatment of diseases, and a lipid-based lipid structure 2 that is bonded to a portion of the outer surface of the nanoparticle 1, thus improving the cellular uptake of the nanoparticle 1.

The nanoparticles 1 are taken into cells to be used for the treatment of diseases, and include a material capable of carrying a drug or treating diseases. Various conventional nanoparticles may be taken into cells to be used for the treatment of disease. Examples thereof may include albumin nanoparticles carrying drugs (concept including siRNA), biodegradable polymer nanoparticles carrying drugs, and siRNA nanoparticles that inhibit the expression of specific proteins. The nanoparticles may have, for example, a diameter of 100 to 300 nm and a spherical shape. The nanoparticles may include a chemical reactive group (hereinafter, referred to as 'first reactive group') that is bonded to the lipid structure. For example, the first reactive group may be a compound containing a thiol group, an amine group, an amino group, or a carboxyl group.

The lipid structure 2 is a lipid-based structure that is bonded to a portion of the outer surface of the nanoparticle 1, thus improving the cellular uptake of the nanoparticle 1. The lipid structure may have, for example, a length of 50 to 300 nm and a width of 3 to 20 nm, and one or more lipid structures may be bonded to the outer surface of the nanoparticle. Further, the lipid structure may include a chemical reactive group (hereinafter, referred to as 'second reactive group') that is chemically bonded to the first reactive group of the nanoparticle. For example, the second reactive group may be a compound containing a thiol group, an amine group, an amino group, or a carboxyl group.

The lipid structure may have, for example, a long tube shape in which a lipid head 21 having hydrophilicity is positioned at an outer side thereof and a lipid tail 22 having hydrophobicity is positioned at an inner side thereof. The second reactive group positioned at one end of the lipid structure having a tube shape is chemically bonded to the first reactive group of the nanoparticle, so that the lipid structure having a tube shape is bonded to the outer surface of the nanoparticle 1. For example, when the nanoparticles are albumin nanoparticles and when an NHS (N-hydroxysuccinimide) reactive group is formed in the lipid structure, the nanoparticle 1 and the lipid structure 2 may be bonded to each other through an NHS-amine reaction. In the present disclosure, surfaces of nanoparticles may be modified with a lipid-based material having high stability and excellent biocompatibility, thereby dramatically improving cellular uptake. The mechanism by which nanoparticles having a size of 100 to 200 nm are taken into cells is endocytosis. In the nanoparticle complex, the lipid structure having a tube shape may be bonded to a portion of the surface of the nanoparticle, so that the nanoparticle complex undergoes endocytosis, directly penetrates a cell membrane, and is effectively taken into spheroid-type tumor cells, thus being applied to a living body model.

A method of manufacturing a nanoparticle complex according to another embodiment of the present disclosure will be described. The method of manufacturing the nanoparticle complex includes a nanoparticle-forming step of forming nanoparticles including a first reactive group, a lipidome-forming step of forming lipid-based lipidomes (such as bubbles and liposomes) having a micro size including a second reactive group chemically bonded to the first reactive group, a lipid-complex-forming step of mixing the nanoparticles and the lipidomes so that the first reactive group and the second reactive group are bonded to each other, thus forming a lipidome-nanoparticle complex in which the nanoparticles are bonded to outer sides of the lipidomes, and a crushing formation step of applying mechanical force to the lipidome-nanoparticle complex formed in the lipid-complex-forming step so that the lipidomes are crushed to form a lipid structure bonded to a portion of the outer surface of the nanoparticle.

The nanoparticle-forming step is a step of forming the nanoparticles so that the nanoparticles taken into cells to be used for the treatment of diseases include the first reactive group. Various conventional methods of manufacturing nanoparticles may be used. For example, in the case of the albumin nanoparticles carrying drugs, an amine group is present in the albumin, so the amine group may be used as a first reactive group. In the case of siRNA nanoparticles that inhibit the expression of specific proteins, the siRNA nanoparticles may be coated with hyaluronic acid to which amine is attached, thus forming a first reactive group in the siRNA nanoparticles.

The lipidome-forming step is a step of forming the lipid-based lipidomes (such as bubbles and liposomes) having a micro size including the second reactive group chemically bonded to the first reactive group. For example, the bubbles are formed of lipids (for example, phospholipids) and are filled with gas, and the second reactive group is positioned on the outer surface of the bubbles. Micro-sized bubbles which contain gas therein and which are in the form of a liposome including phospholipids may be manufactured using a conventional manufacturing method. For example, the phospholipids that are bonded to the second reactive group and the phospholipids that are not bonded to the second reactive group may be mixed at a predetermined ratio in an organic solvent to form a lipid film. The lipid film may be dissolved in a solvent and gas may be injected thereinto, thus forming the bubbles.

The lipid-complex-forming step is a step of mixing the nanoparticles and the lipidomes so that the first reactive group and the second reactive group are bonded to each other, thus forming the lipidome-nanoparticle complex in which the nanoparticles are bonded to outer sides of the lipids.

The crushing formation step is a step of applying mechanical force to the lipidome-nanoparticle complex formed in the lipid-complex-forming step so that the lipidomes are crushed to form the lipid structure bonded to a portion of the outer surface of the nanoparticle. When mechanical force is applied to the lipidome-nanoparticle complex using an ultrasonic device and maintained for a predetermined period of time, the lipidomes are crushed and phospholipids forming the lipidomes are recombined, thus forming the lipid structure having a tube shape bonded to the nanoparticle. In the present disclosure, a top-down process is used, in which the lipid structure is not directly attached to the nanoparticles, lipid-based lipidomes are bonded to the nanoparticles, and mechanical force is applied thereto to thus crush the lipidomes, so that the lipid structure is formed on the surface of the nanoparticles. Accordingly, it is possible to easily mass-produce the nanoparticle complex.

MODE FOR DISCLOSURE

Hereinafter, the present disclosure will be described in more detail through Examples. However, these are only for describing the present disclosure in more detail, and the scope of the present disclosure is not limited thereto.

<Example 1> Manufacture of Nanoparticle Complex

1. Formation of Nanoparticles (NPs)

After albumin (human serum albumin) was dissolved in distilled water at a concentration of 20 mg/mL, the pH was adjusted to 8 using 0.2M NaOH, thus preparing an albumin solution. 100% ethanol was applied at a rate of 1 mL/min, thus titrating the albumin solution. Thereafter, 10 μL of 4% glutaraldehyde was added thereto, ethanol was removed overnight in the dark, and centrifugation was performed under the conditions of 13200 rpm and 10 minutes. Non-particulate albumin was removed using a pipette and re-dispersion was performed with PBS, followed by centrifugation under the conditions of 3000 rpm and 5 minutes. Thereafter, a supernatant (nanoparticles (NPs)) other than micropellets was obtained using a pipette. (Meanwhile, when a fluorescence experiment was performed, a fluorescent dye and nanoparticles were reacted with each other as necessary at room temperature overnight, centrifugation was performed under the conditions of 13200 rpm and 10 minutes, unreacted fluorescent dye was removed using a pipette, and redispersion was performed with PBS for use thereof.)

2. Formation of Liposome

Lipid DSPC (1,2-distearoyl-sn-glycero-3-phosphocholine) and DSPE-PEG-NHS2000 (1,2-distearoyl-sn-glycero-3-phosphoethanolamine-N-polyethylene glycol succinimidyl ester) were mixed at a molar ratio of 9.25:0.75 to be dissolved at a concentration of 10 mg/ml in chloroform. The resultant solution was put into a 1 c vial in an amount of 100 ul so that the concentration thereof was 1 mg/ml. After the chloroform was removed using nitrogen gas, drying was performed for one hour or more using a desiccator while a vacuum was formed, thus forming a lipid film. 1 ml of auto PBS was put into a lipid film vial to form a lipid solution, and the HPLC vial containing the lipid solution was put into water at a temperature of 55° C. or higher so that the temperature of the lipid solution was 55° C. or higher. Sonication was performed in a sonic bath for about 15 seconds (a process of immersion in hot water and a sonication process were repeated about three times), thus forming liposomes.

3. Formation of Bubbles Using Lipids

The resultant materials obtained from the processes of Examples 1 and 2 were mixed with $C_3F_8$ gas, which filled a vial for 30 seconds, using a vial mixer for 45 seconds, thus forming lipid-based bubbles including an NHS reactive group.

4. Formation of Nanoparticle Complex (Directional LT-NPs)

(1) The nanoparticles formed in item 1 of Example 1 were put into a liposome solution (formed by mixing the liposome formed in item 2 of Example 1 with PBS at a concentration of 1 mg/ml) and then reacted at room temperature for 2 hours or more in order to induce an NHS-amine reaction (for forming a liposome-nanoparticle complex (liposome-NPs)). Then, mechanical force was applied for 5 minutes or more under conditions of 2 W, 1 MHz, and a 100% duty cycle using an ultrasonic device. Thereafter, incubation was performed at room temperature for one hour or more so that the crushed liposomes sufficiently formed the lipid structure, thus forming a nanoparticle complex (directional LT-NPs) in which the lipid structure was bonded to a portion of the outer surface of the nanoparticle.

(2) A nanoparticle complex (directional LT-NPs) in which a lipid structure was bonded to a portion of the outer surface of the nanoparticle was formed using the same conditions as in (1) of item 4 of Example 1, except that the bubbles formed in item 3 of Example 1 were used instead of the liposomes.

<Example 2> Confirmation of Characteristics of Nanoparticle Complex

1. The nanoparticles (NPs) formed in item 1 of Example 1 and the nanoparticle complex (directional LT-NPs) formed in (2) of item 4 of Example 1 were subjected to TEM measurement, and the results are shown in FIG. 2. The nanoparticle complex and the lipid structure were subjected to Cryo-TEM measurement, and the results are shown in FIGS. 3 and 4.

2. Referring to FIG. 2, it can be seen that the surface is smooth in the case of nanoparticles, but in the case of the nanoparticle complex, the lipid structure is attached to the surface of the nanoparticles, so the surface thereof is not smooth. Further, referring to FIG. 3, it can be seen that the lipid structure having a tube shape is attached to the surface of the nanoparticles. Referring to FIG. 4, it can be seen more clearly that the lipid structure has a tube shape. Further, referring to FIGS. 3 and 4, it can be seen that the nanoparticles have a diameter of 100 to 300 nm, the lipid structure has a length of 50 to 300 nm and a width of 3 to 20 nm, and one or more lipid structures may be bonded to the outer surface of each nanoparticle.

<Example 3> Evaluation of Cell Uptake Efficiency of Nanoparticle Complex

1. In order to evaluate the cell uptake efficiency of the nanoparticles (NPs) formed in item 1 of Example 1 and the nanoparticle complex (directional LT-NPs) formed in (2) of item 4 of Example 1, analysis was performed using flow cytometry, and the results are shown in FIG. 5. Imaging was performed using a confocal microscope, and the results are shown in FIG. 6. In the analysis that was performed using flow cytometry, A549 cells ($1\times10^4$) were treated with the nanoparticles and a nanoparticle complex labeled with an Alexa 488 fluorescent dye. In the analysis performed using the confocal microscope, A549 cells ($1\times10^5$) in which nuclei were stained using DAPI and in which a cytoskeleton was stained using phalloidin were treated with the nanoparticles and the nanoparticle complex labeled with a Cy5.5 fluorescent dye.

2. Further, in order to evaluate the cell uptake efficiency of the nanoparticles (NPs) formed in item 1 of Example 1 and the liposome-nanoparticle complex (liposome-NPs) and the nanoparticle complex (directional LT-NPs) formed in (1) of item 4 of Example 1, imaging was performed using a confocal microscope, and the results are shown in FIG. 7. In the analysis that was performed using the confocal microscope, A549 cells ($1\times10^5$) in which nuclei were stained using DAPI were treated with the nanoparticles, liposome-nanoparticle complex, and nanoparticle complex labeled with an Alexa 555 fluorescent dye.
3. Referring to FIG. 5, it can be seen that the nanoparticle complex has significantly superior cell uptake efficacy compared to the nanoparticles. Referring to FIG. 6, it can be seen that more of the red color is observed in the cell when the nanoparticle complex is used instead of the nanoparticles. Accordingly, in the experiment using fluorescence images, the same results as in FIG. 5 can be confirmed. Further, referring to FIG. 7, it can be confirmed that the nanoparticle complex has significantly superior cell uptake efficacy compared to the nanoparticles or the liposome-nanoparticle complex. Accordingly, it can be seen that the nanoparticle complex is formed not only using bubbles including lipids but also using liposomes or other lipid spheres.

<Example 4> Evaluation of Cell Uptake Efficiency of Nanoparticle Complex after Treatment with Endocytosis Inhibitor 1. With respect to the cells treated with an endocytosis inhibitor, the cell uptake efficiency of the nanoparticles (NPs) formed in item 1 of Example 1 and the nanoparticle complex (directional LT-NPs) formed in (2) of item 4 of Example 1 was evaluated. It is known that 200 nm-sized nanoparticles undergo endocytosis based on a total of three mechanisms: macropinocytosis, clarthrin-independent endocytosis, and clarthrin-dependent endocytosis.

Accordingly, an inhibitor for inhibiting endocytosis was selected to treat A549 cells ($1\times10^4$) for one hour individually or simultaneously, and the cells were then treated with the nanoparticles and nanoparticle complex labeled with an Alexa 488 fluorescent dye for three hours, followed by measurement using flow cytometry. The measurement results were normalized based on the nanoparticles and are shown in FIG. 8. EIPA (5-(N-ethyl-N-isopropyl)amiloride) was selected as a macropinocytosis inhibitor (at a concentration of 25 ug/ml) to inhibit a Na+/H+ exchange mechanism. CPZ (chlorpromazine) was selected as a clathrin-dependent endocytosis inhibitor (at a concentration of 20 ug/ml) to inhibit inhibits-clathrin-coated pit formation. MβCD (methyl-β-cyclodextrin) was selected as a clathrin-independent endocytosis inhibitor (a concentration of 3 mg/ml) to inhibit a cholesterol-dependent endocytic process.

2. Referring to FIG. 8, it can be seen that the cell uptake efficacy is greatly reduced due to the CPZ and EIPA inhibitors in the case of the nanoparticles (NPs), and that when treatment with the three types of inhibitors was performed to inhibit all of the endocytosis mechanisms, uptake of the nanoparticles into the cells hardly occurred. In the case of the nanoparticle complex (directional LT-NPs), it can be confirmed that the cell uptake efficacy thereof is about 350% better than that of the nanoparticles. Even when the three types of inhibitors were used to inhibit all of the endocytosis mechanisms, it can be observed that the cell uptake efficacy thereof is excellent compared to the case of the nanoparticles. Accordingly, it can be confirmed that the nanoparticle complex not only undergoes endocytosis, but also directly penetrates a cell membrane.

<Example 5> Evaluation of Efficacy of Nanoparticle Complex as Anticancer Drug Delivery System 1. The same procedure as in item 1 of Example 1 and in (2) of item 4 of Example 1 was performed, except that a solution mixed with doxorubicin was added to an albumin solution to perform a reaction and ethanol titration was then performed until the mixed solution became cloudy, thereby forming nanoparticles containing doxorubicin and a nanoparticle complex containing doxorubicin. MCF-7/ADR, which was a breast-cancer-cell strain having anticancer resistance, was seeded in well plates, and each of the media containing doxorubicin (100 mM, DOX), doxorubicin-containing nanoparticles (containing 100 mM doxorubicin), and a doxorubicin-containing nanoparticle complex (containing 100 mM doxorubicin) was incubated at 37° C. for 6 hours. Then, the cell strains were incubated in normal media for 48 hours to evaluate cell vialbilty, and the results are shown in FIG. 9. For cell viability, an MTT assay and a trypan-blue-dye-exclusion method were used. The cells having a 0.4% trypan blue dye were incubated, followed by counting with a Neubauer hemocytometer, thereby determining cell viability. In the MTT assay, 96-well plates and 1.5 mg/ml of an MTT reagent (3-(4,5-dimethylthiazol-2yl)-2,5-diphenyltetrazolium bromide) were used, incubation with 15 μl of the MTT reagent was performed for 2 hours, and 200 μl of DMSO was added to each well. The resulting culture plates were measured at 570 nm using a plate reader (Bio Tek Instruments, Inc, Winooski, VT, USA).
2. Referring to FIG. 9, it can be seen that when breast cancer cells were treated with doxorubicin at the same concentration, in the case in which the nanoparticle complex was used, the apoptosis effect of the anticancer drug was increased not only in general cancer cells, but also in cells having resistance to the anticancer drug.

<Example 6> Evaluation of Nanoparticle Complex as a Genome Drug Delivery System

1. Albumin (human serum albumin) was dissolved in 0.1 mM HEPES with 0.01 mM EDTA so that the concentration was 40 mg/mL, and a thiol-modify VEGF siRNA duplex (5' modified) was then added thereto. After titration was performed using 100% ethanol applied at a rate of 1 mL/min until the solution including albumin and siRNA mixed therein became cloudy, ethanol was removed overnight in the dark, and centrifugation was performed under the conditions of 13200 rpm and 10 minutes. Nonparticulate albumin and unreacted drug were removed using a pipette and re-dispersion was performed with PBS, followed by centrifugation under the conditions of 3000 rpm and 5 minutes. Thereafter, a supernatant (nanoparticles carrying siRNA (siRNA NPs)) other than micropellets was obtained using a pipette. The sense of the thiol-modify VEGF siRNA duplex is 5'-AUGUGAAUGCAGAC-CAAAGAA-3' (SEQ ID NO: 1), and the antisense thereof is 5'-thiol-UUCUUUGGUCUGCAUUCA-CAU-3' (SEQ ID NO: 2).
2. The nanoparticles carrying siRNA formed in item 1 of Example 6 were put into a bubble solution (formed by mixing the bubbles formed in item 3 of Example 1 with PBS at a concentration of 1 mg/ml), and then reacted at room temperature for 2 hours or more. Mechanical force was applied for 5 minutes or more under conditions of 2 W, 1 MHz, and a 100% duty cycle using an ultrasonic device. Thereafter, incubation was performed at room temperature for one hour or more so that the crushed bubbles sufficiently formed the lipid structure, thus forming a nanoparticle complex carrying siRNA (directional siRNA LT-NPs) in which a lipid structure was bonded to a portion of the outer surface of a nanoparticle carrying siRNA.

3. The gene silencing of the siRNA NPs and directional siRNA LT-NPs in items 1 and 2 of Example 6 is confirmed and shown in FIGS. 9 and 10. In confirmation of the gene silencring, MCF-7 cells (1×10$^5$) were treated with each of the siRNA NPs and the directional siRNA LT-NPs for 3 hours. After incubation for 24 hours, mRNA was extracted, and PCR was performed on cells in the same manner. In a PCR gel retardation assay, gene bands were stained with a GelRed-nucleic-acid stain and visualized using a Gel-Doc-imaging device. FIG. 10 shows a value obtained by quantifying the relative intensity of the gene band using Image Pro.

4. Referring to FIGS. 9 and 10, it can be confirmed that the gene silencing efficiency is much better when using the directional siRNA LT-NPs than when using the siRNA NPs. Accordingly, it can be seen that the nanoparticle complex may be effectively used as a genome drug delivery system.

<Example 7> Evaluation of Efficacy in Tumor Cell Spheroid

1. Unlike general adherent cancer cells, a tumor cell spheroid proliferates in a 3D culture. In the case of a spheroid, cancer cells grow in a floating state on a medium, so the cancer cells grow while aggregating. There is a research result that the form that grows in an aggregation state mimics the extracellular matrix (ECM) of cancer tissue, so an experiment was conducted in this model in order to confirm in vitro whether tissue penetration occurred due to the modification of lipid surfaces.

2. Formation of Spheroid Cells

After 10 g of poly(2-hydroxyethyl methacrylate) was added to 1 L of 100% pure ethanol and dissolved at 60° C. therein, 3.3 ml of dissolved poly(2-hydroxyethyl methacrylate) based on 100 phi was evenly dispersed over the entire plate and then dried for 24 hours to perform coating. MCF7 cells were seeded on the plate prepared as described above and maintained for 5 days, thus obtaining cells in which spheroids were formed.

3. Treatment of Spheroid Cells with Nanoparticle Complex (1) In order to evaluate the spheroid-cell-uptake efficiency of the nanoparticles (NPs) formed in item 1 of Example 1 and the nanoparticle complex (directional LT-NPs) formed in (2) of item 4 of Example 1, imaging was performed using a confocal microscope, and the results are shown in FIG. 12. Spheroid-type MCF-7 cells (1×10$^5$), in which the nuclei were stained using DAPI and which were formed in item 2 of Example 7, were treated with the nanoparticles and nanoparticle complex labeled with an Alexa 555 fluorescent dye. After 3 hours, measurement using a confocal microscope was performed.

(2) Referring to FIG. 11, it can be confirmed that cell uptake efficiency is better in the nanoparticle complex than in the nanoparticles. Accordingly, it can be confirmed that the uptake efficiency of the nanoparticle complex is excellent not only in a simple in-vitro environment, but also in a simulated in-vivo environment. Therefore, it can be seen that the nanoparticle complex exhibits excellent tissue penetration efficiency.

In the above, the applicant has described various embodiments of the present disclosure, but such embodiments are only one embodiment that implements the technical idea of the present disclosure, and any change or modification should be construed as falling within the scope of the present disclosure as long as the technical idea of the present disclosure is implemented.

The invention claimed is:

1. A method of manufacturing a nanoparticle complex, the method comprising:
- a nanoparticle-forming step of forming nanoparticle including a first reactive group;
- a liposome-forming step of forming phospholipid-based liposome having a micro size including a second reactive group for bonding chemically to the first reactive group;
- a nanoparticle complex forming step of mixing the nanoparticle and the liposome so that the first reactive group and the second reactive group are bonded to each other, thus forming the nanoparticle complex in which the nanoparticles are bonded to outer sides of the liposome; and
- a crushing formation step of applying mechanical force to the nanoparticle complex formed so that the liposome is crushed to form a lipid structure bonded to a portion of an outer surface of the nanoparticle, thus manufacturing the nanoparticle complex, wherein the nanoparticle is taken into cells to be used for treatment of diseases, and the lipid structure improves a cellular uptake of the nanoparticle, wherein the nanoparticle has a diameter of 100 to 300 nm, and the lipid structure has a length of 50 to 300 nm and a width of 3 to 20 nm.

2. The method of claim 1, wherein in the crushing formation step, the mechanical force is applied to the nanoparticle complex and maintained for a predetermined period of time, so that the liposome is crushed and phospholipids forming the liposome is recombined, thus forming the lipid structure having a tube shape bonded to the nanoparticle.

* * * * *

SEQUENCE LISTING

<160> NUMBER OF SEQ ID NOS: 2

<210> SEQ ID NO 1
<211> LENGTH: 21
<212> TYPE: RNA
<213> ORGANISM: Artificial Sequence
<220> FEATURE:
<223> OTHER INFORMATION: sense of siRNA

<400> SEQUENCE: 1
augugaaugc agaccaaaga a                    21

<210> SEQ ID NO 2
<211> LENGTH: 21
<212> TYPE: RNA
<213> ORGANISM: Artificial Sequence
<220> FEATURE:
<223> OTHER INFORMATION: antisense of siRNA

<400> SEQUENCE: 2
uucuuugguc ugcauucaca u                    21